United States Patent [19]

Dohmen et al.

[11] Patent Number: 6,075,023
[45] Date of Patent: Jun. 13, 2000

[54] METHOD FOR COMBATTING FISH MYCOSES AND ONE-CELLED ECTOPARASITES

[75] Inventors: Gerhard Peter Dohmen, Weinheim; Christoph Künast, Otterstadt; Reinhart Munk; Gerhard Rothhaas, both of Limburgerhof, all of Germany

[73] Assignee: BASF Aktiengesellschaft, Ludwigshafen, Germany

[21] Appl. No.: 09/011,712

[22] PCT Filed: Jul. 30, 1996

[86] PCT No.: PCT/EP96/03354

§ 371 Date: Feb. 17, 1998

§ 102(e) Date: Feb. 17, 1998

[87] PCT Pub. No.: WO97/06690

PCT Pub. Date: Feb. 27, 1997

[30] Foreign Application Priority Data

Aug. 17, 1995 [DE] Germany .................. 195 30 175

[51] Int. Cl.[7] .................. A01N 43/66; A01N 43/64; A01N 43/40; A01N 43/58; A01N 43/54; A01N 43/82; A01N 43/76; A01N 43/80; A01N 43/50; A01N 43/56; A01N 43/36; A01N 43/32; A01N 47/10; A01N 37/00; A01N 37/18; A01N 33/24; A01N 43/08; A01N 33/02

[52] U.S. Cl. .................. 514/241; 514/242; 514/245; 514/277; 514/247; 514/256; 514/269; 514/272; 514/336; 514/344; 514/345; 514/348; 514/349; 514/351; 514/352; 514/357; 514/365; 514/369; 514/370; 514/374; 514/376; 514/377; 514/378; 514/380; 514/383; 514/384; 514/396; 514/398; 514/399; 514/400; 514/403; 514/406; 514/407; 514/422; 514/423; 514/425; 514/426; 514/428; 514/436; 514/476; 514/478; 514/506; 514/529; 514/613; 514/617; 514/618; 514/619; 514/620; 514/622; 514/640; 514/649; 514/461; 514/472; 514/473

[58] Field of Search .................. 514/640, 241, 514/242, 245, 461, 472, 473, 483, 406, 407, 396, 398, 399, 400, 374, 376, 377, 380, 365, 369, 370, 336, 247, 256, 269, 272, 436, 383, 384, 277, 344–5, 348–9, 351–2, 357, 422–3, 425.6, 428; 564/265

[56] References Cited

U.S. PATENT DOCUMENTS

| | | | |
|---|---|---|---|
| 3,152,953 | 10/1964 | Strong et al. | 167/46 |
| 4,826,842 | 5/1989 | Mehlhorn et al. | 514/241 |
| 4,829,085 | 5/1989 | Wenderoth et al. | 514/522 |
| 4,959,484 | 9/1990 | Daum et al. | 549/334 |
| 5,057,501 | 10/1991 | Thornfeldt | 514/53 |

FOREIGN PATENT DOCUMENTS

| | | |
|---|---|---|
| 167 710 | 3/1985 | European Pat. Off. |
| 9603047 | 2/1996 | WIPO. |
| 9603047 A1 | 2/1996 | WIPO. |

OTHER PUBLICATIONS

Clough, *Natural Product Reports*, 1993, pp. 565–574.

Roehl et al., *Biochem. Soc. Trans.*, vol. 22, 1993, p. 63S.

Kohle et al., *Biochem. Soc. Trans.*, vol. 22, 1993, p. 65S.

*Chem. Abst.*, vol. 96, No. 13, 1982, Abs. No. 99524r.

*Primary Examiner*—S. Mark Clardy
*Assistant Examiner*—Alton Pryor
*Attorney, Agent, or Firm*—Keil & Weinkauf

[57] ABSTRACT

Fish mycoses and single-cell ectoparasites on fish are controlled using an active compound suitable for inhibiting the mitochondrial respiratory chain at the stage of the $b/c_1$ complex.

2 Claims, No Drawings

METHOD FOR COMBATTING FISH MYCOSES AND ONE-CELLED ECTOPARASITES

This application is a 371 of PCT/EP96/03354 filed Jul. 30, 1996.

The present invention relates to a method for controlling fish mycoses and single-cell ectoparasites on fish, which comprises using an active compound suitable for inhibiting the mitochondrial respiratory chain at the stage of the $b/c_1$ complex.

The invention additionally relates to compounds of the formula IA or IB

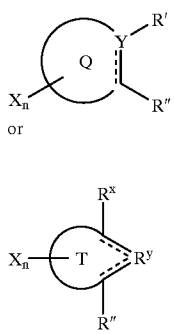

where ⋯ is a single or double bond and the index and the substituents have the following meanings:

R' is —C[CO$_2$CH$_3$]=CHOCH$_3$, —C[CO$_2$CH$_3$]=NOCH$_3$, —C[CONHCH$_3$]=NOCH$_3$, —C[CO$_2$CH$_3$]=CHCH$_3$, —C[CO$_2$CH$_3$]=CHCH$_2$CH$_3$, —C[COCH$_3$]=NOCH$_3$, —C[COCH$_2$CH$_3$]=NOCH$_3$, —N(OCH$_3$)—CO$_2$CH$_3$, —N(CH$_3$)—CO$_2$CH$_3$, —N(CH$_2$CH$_3$)—CO$_2$CH$_3$,

R" is a C-organic radical,
 a C-organic radical which is bonded directly or via an oxy, mercapto, amino or alkylamino group, or
 together with a group X and the ring Q or T, to which they are bonded, are an unsubst. or subst. bicyclic, partially or completely unsaturated system which, in addition to carbon ring members, can contain heteroatoms from the group consisting of oxygen, sulfur and nitrogen, R$^x$ is —OC[CO$_2$CH$_3$]=CHOCH$_3$, —OC[CO$_2$CH$_3$]=CHCH$_3$, —OC[CO$_2$CH$_3$]=CHCH$_2$CH$_3$, —SC[CO$_2$CH$_3$]=CHOCH$_3$, —SC[CO$_2$CH$_3$]=CHCH$_3$, —SC[CO$_2$CH$_3$]=CHCH$_2$CH$_3$, —N(CH$_3$)C[CO$_2$CH$_3$]=CHOCH$_3$, —N(CH$_3$)C[CO$_2$CH$_3$]=NOCH$_3$, —CH$_2$C[CO$_2$CH$_3$]=CHOCH$_3$, —CH$_2$C[CO$_2$CH$_3$]=NOCH$_3$, —CH$_2$C[CONHCH$_3$]=NOCH$_3$, R$^y$ is oxygen, sulfur, =CH— or =N—, n is 0, 1, 2 or 3, where the radicals X can be different if n>1;

X is cyano, nitro, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio or, in the case where n>1, a C$_3$–C$_5$-alkylene, C$_3$–C$_5$-alkenylene, oxy-C$_2$–C$_4$-alkylene, oxy-C$_1$–C$_3$-alkylenoxy, oxy-C$_2$–C$_4$-alkenylene, oxy-C$_2$–C$_4$-alkenylenoxy or butadienediyl group bonded to two adjacent C atoms of the phenyl ring, where these chains in turn can carry one to three of the following radicals: halogen, C$_1$–C$_4$-alkyl, C$_1$–C$_4$-haloalkyl, C$_1$–C$_4$-alkoxy, C$_1$–C$_4$-haloalkoxy or C$_1$–C$_4$-alkylthio, Y is =C— or —N—, Q is phenyl, pyrrolyl, thienyl, furyl, pyrazolyl, imidazolyl, oxazolyl, isoxazolyl, thiazolyl, thiadiazolyl, triazolyl, pyridinyl, 2-pyridonyl, pyrimidinyl or triazinyl, T is phenyl, oxazolyl, thiazolyl, thiadiazolyl, oxadiazolyl, pyridinyl, pyrimidinyl or triazinyl, as an antimycotic, and compositions comprising these compounds suitable for controlling fish mycoses and for controlling single-cell ectoparasites and costiasis.

To date, only a few substances are known which are suitable for controlling fish mycoses and single-cell ectoparasites.

The preparation Malachite Green used mainly until now had to be taken off the market because of its teratogenicity [cf. Meyer et al., *Transactions of the American Fisheries Society*, 112, 818–824] and suspicion of carcinogenicity. Other products (eg. formalin, potassium permanganate, sodium chloride) are only slightly active and in some cases have undesirably severe effects on the environment. Regarding the existing possibilities of controlling fish parasites, see W. Schaperclaus, Fischkrankheiten (2nd part), 4th edition, Akademie-Verlag Berlin, 1979 and H.-H. Reichenbach-Klinke, Reichenbach-Kline's Fish Pathology, T.S.H. Publications Inc. Ltd., 1973.

Active compounds which inhibit the mitochondrial respiratory chain at the stage of the $b/c_1$ complex are known from the literature as fungicides [cf. Dechema monographs Vol. 129, 27–38, VCH Verlagsgemeinschaft Weinheim 1993; Natural Product Reports 1993, 565–574; Biochem. Soc. Trans. 22, 63S (1993)].

In particular, representatives of the active compounds of the formula I (or IA and IB) having fungicidal and in some cases also bioregulatory action are described in the following patents:

EP-A 178 826, EP-A 203 606, EP-A 203 608, EP-A 206 523,
EP-A 212 859, EP-A 226 917, EP-A 226 974, EP-A 242 070,
EP-A 242 081, EP-A 243 012, EP-A 243 014, EP-A 251 082,
EP-A 253 213, EP-A 254 426, EP-A 256 667, EP-A 260 794,
EP-A 260 832, EP-A 267 734, EP-A 273 572, EP-A 274 825,
EP-A 278 595, EP-A 280 185, EP-A 291 196, EP-A 299 694,
EP-A 307 101, EP-A 307 103, EP-A 310 954, EP-A 312 221,
EP-A 312 243, EP-A 329 011, EP-A 331 966, EP-A 335 519,
EP-A 336 211, EP-A 337 211, EP-A 341 845, EP-A 350 691,
EP-A 354 571, EP-A 363 818, EP-A 370 629, EP-A 373 775,
EP-A 374 811, EP-A 378 308, EP-A 378 755, EP-A 379 098,
EP-A 382 375, EP-A 383 117, EP-A 384 211, EP-A 385 224,
EP-A 385 357, EP-A 386 561, EP-A 386 681, EP-A 389 901,
EP-A 391 451, EP-A 393 428, EP-A 393 861, EP-A 398 692,
EP-A 400 417, EP-A 402 246, EP-A 405 782, EP-A 407 873,
EP-A 409 369, EP-A 414 153, EP-A 416 746, EP-A 420 091,
EP-A 422 597, EP-A 426 460, EP-A 429 968, EP-A 430 471,
EP-A 433 233, EP-A 433 899, EP-A 439 785, EP-A 459 285,
EP-A 460 575, EP-A 463 488, EP-A 463 513, EP-A 464 381,

EP-A 468 684, EP-A 468 695, EP-A 468 775, EP-A 471 261,

EP-A 472 224, EP-A 472 300, EP-A 474 042, EP-A 475 158,

EP-A 477 631, EP-A 480 795, EP-A 483 851, EP-A 483 985,

EP-A 487 409, EP-A 493 711, EP-A 498 188, EP-A 498 396,

EP-A 499 823, EP-A 503 436, EP-A 508 901, EP-A 509 857,

EP-A 513 580, EP-A 515 901, EP-A 517 301, EP-A 528 245,

EP-A 532 022, EP-A 532 126, EP-A 532 127, EP-A 535 980,

EP-A 538 097, EP-A 544 587, EP-A 546 387, EP-A 548 650,

EP-A 564 928, EP-A 566 455, EP-A 567 828, EP-A 571 326,

EP-A 579 071, EP-A 579 124, EP-A 579 908, EP-A 581 095,

EP-A 582 902, EP-A 582 925, EP-A 583 806, EP-A 584 625,

EP-A 585 751, EP-A 590 610, EP-A 596 254, WO-A 90/07,493,

WO-A 92/13,830, WO-A 92/18,487, WO-A 92/18,494, WO-A 92/21,653,

WO-A 93/07,116, WO-A 93/08,180, WO-A 93/08,183, WO-A 93/15,046,

WO-A 93/16,986, WO-A 94/00,436, WO-A 94/05,626, WO-A 94/08,948,

WO-A 94/08,968, WO-A 94/10,159, WO-A 94/11,334, JP-A 02/121,970,

JP-A 04/182,461, JP-A 05/201,946, JP-A 05/201,980,

JP-A 05/255,012, JP-A 05/294,948, JP-A 06/025,133,

JP-A 06/025,142, JP-A 06/056,756, FR-A 2 670 781, GB-A 2 210 041,

GB-A 2 218 702, GB-A 2 238 308, GB-A 2 249 092, GB-A 2 253 624,

GB-A 2 255 092, DE-A 39 05 911, EP-A 686 152, EP-A 691 950,

EP-A 627 411, EP-A 647 631, WO-A 95/21,156, WO-A 95/21,153,

WO-A 95/21,154, EP-A 673 923.

It is an object of the present invention to provide compositions for controlling fish mycoses and single-cell ectoparasites on fish which have good activity, are not concentrated in the fish to an undesired extent and have no unacceptable effects on the biotic communities.

We have found that this object is achieved by the compositions defined at the outset.

Fundamentally all active compounds described in the patents mentioned at the outset are suitable for the provision of the compositions according to the invention, where in particular the compounds mentioned in the examples given there are to be taken into account. Of particular importance in this case are compounds of the formulae IA and IB

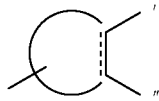

-continued

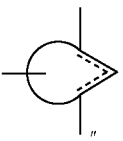

where R" is one of the following groups:
unsubst. or subst. aryloxy, unsubst. or subst. hetaryloxy, unsubst. or subst. aryloxymethylene, unsubst. or subst. hetaryloxymethylene, unsubst. or subst. arylethenylene, unsubst. or subst. hetarylethenylene, or a group $R^{\alpha}R^{\beta}C{=}NOCH_2{-}$ or $R^{\gamma}ON{=}CR^{\delta}CR^{\epsilon}{=}NOCH_2$ where the radicals $R^{60}$, $R^{\beta}$, $R^{\gamma}$, $R^{67}$ and $R^{68}$ in general and in particular have the meanings described in the following patents:

EP-A 370 629, EP-A 414 153, EP-A 426 460, EP-A 460 575,

EP-A 463 488, EP-A 472 300, EP-A 498 188, EP-A 498 396,

EP-A 515 901, EP-A 585 751, WO-A 90/07,493, WO-A 92/13,830,

WO-A 92/18,487, WO-A 92/18,494, WO-A 93/15,046, WO-A 93/16,986,

WO-A 94/08,948, WO-A 94/08,968, JP-A 05/201,946, JP-A 05/255,012,

JP-A 05/294,948, JP-A 06/025,133, JP-A 06/025,142,

WO-A 95/21,153 and WO-A 95/21,154.

Particularly preferred unsubst. or subst. aryloxy or unsubst. or subst. hetaryloxy radicals correspond in general and in particular to the meanings described in the following patents:

EP-A 178 826, EP-A 242 070, EP-A 242 081, EP-A 253 213,

EP-A 254 426, EP-A 256 667, EP-A 260 794, EP-A 280 185,

EP-A 307 103, EP-A 341 845, EP-A 382 375, EP-A 393 861,

EP-A 398 692, EP-A 405 782, EP-A 430 471, EP-A 468 684,

EP-A 468 695, EP-A 477 631, EP-A 483 985, EP-A 498 188,

EP-A 513 580, EP-A 515 901, WO-A 93/15,046, WO-A 94/10,159,

GB-A 2 253 624 and JP-A 04/182,461.

Particularly preferred unsubst. or subst. aryloxymethylene or unsubst. or subst. hetaryloxymethylene radicals correspond in general and in particular to the meanings described in the following patents:

EP-A 178 826, EP-A 226 917, EP-A 253 213, EP-A 254 426, EP-A 278 595, EP-A 280 185, EP-A 299 694, EP-A 335 519, EP-A 350 691, EP-A 363 818, EP-A 373 775, EP-A 378 308, EP-A 385 224, EP-A 386 561, EP-A 398 692, EP-A 400 417, EP-A 407 873, EP-A 472 224, EP-A 477 631, EP-A 498 188, EP-A 498 396, EP-A 513 580, EP-A 515 901, EP-A 579 124, WO-A 93/08,180, WO-A 93/15,046, WO-A 94/00,436, JP-A 04/182,461, EP-A 686 152, EP-A 673 923 and WO-A 95/29,896.

Particularly preferred unsubst. or subst. arylethenylene or unsubst. or subst. hetarylethenylene radicals correspond in general and in particular to the meanings described in the following patents:

EP-A 178 826, EP-A 203 606, EP-A 253 213, EP-A 254 426, EP-A 280 185, EP-A 378 755, EP-A 398 692, EP-A 402 246, EP-A 474 042, EP-A 475 158, EP-A 477 631, EP-A 487 409, EP-A 498 188, EP-A 498 396, EP-A 513 580, EP-A 515

901, EP-A 528 245, EP-A 544 587, WO-A 93/15,046, WO-A 94/11,334 and FR-A 2 670 781 and EP-A 691 332.

Particularly preferred active compounds of the formula IA in which R' is —C[CO$_2$CH$_3$]=CHOCH$_3$ correspond in general and in particular to the compounds described in the following patents:

EP-A 178 826, EP-A 203 606, EP-A 226 917, EP-A 242 070, EP-A 242 081, EP-A 256 667, EP-A 260 794, EP-A 278 595, EP-A 299 694, EP-A 307 103, EP-A 335 519, EP-A 341 845, EP-A 350 691, EP-A 370 629, EP-A 373 775, EP-A 378 308, EP-A 378 755, EP-A 382 375, EP-A 385 224, EP-A 386 561, EP-A 414 153, EP-A 426 460, EP-A 430 471, EP-A 463 488, EP-A 468 695, EP-A 472 224, EP-A 474 042, EP-A 475 158, EP-A 483 985, EP-A 487 409, EP-A 515 901, EP-A 528 245, EP-A 544 587, WO-A 90/07,493, WO-A 92/18,487, WO-A 92/18,494, WO-A 93/08,180, WO-A 93/16,986, WO-A 94/00,436, WO-A 94/08,948, WO-A 94/08,968, WO-A 94/10,159, WO-A 94/11,334, FR-A 2 670 781, JP-A 06/025,133, WO-A 95/21,153 and EP-A 673 923.

Particularly preferred active compounds of the formula IA in which R' is —C[CO$_2$CH$_3$]=NOCH$_3$ correspond in general and in particular to the compounds described in the following patents:

EP-A 253 213, EP-A 254 426, EP-A 299 694, EP-A 363 818, EP-A 378 308, EP-A 385 224, EP-A 386 561, EP-A 400 417, EP-A 407 873, EP-A 460 575, EP-A 463 488, EP-A 468 684, EP-A 472 300, EP-A 515 901, WO-A 94/00,436, WO-A 94/08,948, WO-A 94/10,159, WO-A 94/11,334, JP-A 05/201,946, JP-A 05/255,012, JP-A 05/294,948, WO-A 95/21,153 and EP-A 673 923.

Particularly preferred active compounds of the formula IA in which R' is —C[CONHCH$_3$]=NOCH$_3$ correspond in general and in particular to the compounds described in the following patents:

EP-A 398 692, EP-A 463 488, EP-A 477 631, EP-A 515 901, EP-A 579 124, EP-A 585 751, WO-A 92/13,830, WO-A 93/08,180, WO-A 94/08,948, WO-A 94/10,159, WO-A 94/11,334, GB-A 2 253 624, JP-A 04/182,461, JP-A 05/201, 946, JP-A 05/255,012, JP-A 05/294,948, EP-A 686 152, WO-A 21,154, EP-A 673 923 and EP-A 691 332.

Particularly preferred active compounds of the formula IA in which R' is —C[CO$_2$CH$_3$]=CHCH$_3$ or —C[CO$_2$CH$_3$]=CHCH$_2$CH$_3$ correspond in general and in particular to the compounds described in the following patents:

EP-A 280 185, EP-A 463 488, EP-A 513 580, EP-A 515 901, WO-A 95/21,153, EP-A 673 923 and WO-A 95/29,896.

Particularly preferred active compounds of the formula IA in which R' is —C[COCH$_3$]=NOCH$_3$ or —C[COCH$_2$CH$_3$]=NOCH$_3$ correspond in general and in particular to the compounds described in EP-A 498 188.

Particularly preferred active compounds of the formula IA in which R' is —N(OCH$_3$)—CO$_2$CH$_3$, —N(CH$_3$)—CO$_2$CH$_3$ or —N(CH$_2$CH$_3$)—CO$_2$CH$_3$ correspond in general and in particular to the compounds described in the following patents: EP-A 498 396, WO-A 93/15,046, JP-A 06/025,142 and JP-A 06/056,756.

Particularly preferred active compounds of the formula IB in which R is —OC[CO$_2$CH$_3$]=CHOCH$_3$, —OC[CO$_2$CH$_3$]=CHCH$_3$, —OC[CO$_2$CH$_3$]=CHCH$_2$CH$_3$, —SC[CO$_2$CH$_3$]=CHOCH$_3$, —SC[CO$_2$CH$_3$]=CHCH$_3$, —SC[CO$_2$CH$_3$]=CHCH$_2$CH$_3$, —N(CH$_3$)C[CO$_2$CH$_3$]=CHOCH$_3$, —N(CH$_3$)C[CO$_2$CH$_3$]=NOCH$_3$, —CH$_2$C[CO$_2$CH$_3$]=CHOCH$_3$, —CH$_2$C[CO$_2$CH$_3$]=NOCH$_3$ or —CH$_2$C[CONHCH$_3$]=NOCH$_3$ correspond in general and in particular to the compounds described in the following patents:

EP-A 212 859, EP-A 331 966, EP-A 383 117, EP-A 384 211, EP-A 389 901, EP-A 409 369, EP-A 464 381, EP-A 471 261, EP-A 503 436, EP-A 546 387, EP-A 548 650, EP-A 579 908 and EP-A 584 625.

Examples of particularly suitable active compounds IA and IB are compiled in the following tables.

TABLE I.1A

Compounds of the formula IA, in which Q is phenyl, R' is —C(CO$_2$CH$_3$)=CHOCH$_3$, n has the value 0, R" is unsubst. or subst. (het)aryloxymethylene, where the unsubst. or subst. (het)aryl group has the following meanings

| No. | Unsubst. or subst. (het)aryl | Reference |
|---|---|---|
| I.1A-1 | 2-CH$_3$—C$_6$H$_4$ | EP-A 226 917 |
| I.1A-2 | 2,5-(CH$_3$)$_2$—C$_6$H$_3$ | EP-A 226 917 |
| I.1A-3 | 2-CH$_3$, 4-C[CH$_3$]=NOCH$_3$—C$_6$H$_3$ | EP-A 386 561 |
| I.1A-4 | 2-CH$_2$CH$_2$CH$_3$, 6-CF$_3$-pyrimidin-4-yl | EP-A 407 873 |

TABLE I.1B

Compounds of the formula IA, in which R' is —C(CO$_2$CH$_3$)=CHOCH$_3$, Q is phenyl, n has the value 0, R" is unsubst. or subst. (het)aryloxy, where the unsubst. or subst. (het)aryl group has the following meanings

| No. | Unsubst. or subst. (het)aryl | Reference |
|---|---|---|
| I.1B-1 | C$_6$H$_5$ | EP-A 178 826 |
| I.1B-2 | 6-[2-CN—C$_6$H$_4$—O]-pyrimidin-4-yl | EP-A 382 375 |

TABLE I.1C

Compounds of the formula IA, in which R' is —C(CO$_2$CH$_3$)=CHOCH$_3$, Q is phenyl, n has the value 0, R" is unsubst. or subst. (het)arylethenylene, where die unsubst. or subst. (het)aryl group has the following meanings

| No. | Unsubst. or subst. (het)aryl | Reference |
|---|---|---|
| I.1C-1 | 1-(2,4-Cl$_2$—C$_6$H$_3$), 5-CF$_3$-pyrazol-4-yl | EP-A 528 245 |
| I.1C-2 | 1-(4-Cl—C$_6$H$_4$)-pyrazol-4-yl | EP-A 378 755 |
| I.1C-3 | 3-CF$_3$—C$_6$H$_4$ | EP-A 203 606 |
| I.1C-4 | 3-Cl—C$_6$H$_4$ | EP-A 203 606 |
| I.1C-5 | 4-C$_6$H$_5$—C$_6$H$_4$ | EP-A 203 606 |

TABLE I.1D

Compounds of the formula IA, in which Q is phenyl, R' is —C(CO$_2$CH$_3$)=CHOCH$_3$, n has the value 0, R" is CH$_2$ON=CR$^\alpha$R$^\beta$, where R$^\alpha$ and R$^\beta$ have the following meanings

| No. | R$^\alpha$ | R$^\beta$ | Reference |
|---|---|---|---|
| I.1D-1 | CH$_3$ | 4-Cl—C$_6$H$_4$ | EP-A 370 629 |
| I.1D-2 | CH$_3$ | 3-CF$_3$—C$_6$H$_4$ | EP-A 370 629 |
| I.1D-3 | CH$_3$ | 4-OCH$_2$CH$_3$-pyrimidin-2-yl | WO-A 92/18,487 |

TABLE I.1E

Compounds of the formula IA, in which Q is phenyl, R' is —C(CO$_2$CH$_3$)=CHOCH$_3$, n has the value 0, R" is CH$_2$ON=CR$^\gamma$R$^\delta$=NOR$^\epsilon$, where R$^\gamma$, R$^\delta$ and R$^\epsilon$ have the following meanings

| No. | R$^\gamma$ | R$^\delta$ | R$^\epsilon$ | Reference |
|---|---|---|---|---|
| I.1E-1 | CH$_3$ | CH$_3$ | CH$_3$ | WO-A 95/21,153 |
| I.1E-2 | CH$_3$ | CH$_3$ | CH$_2$CH$_3$ | WO-A 95/21,153 |
| I.1E-3 | CH$_3$ | C$_6$H$_5$ | CH$_3$ | WO-A 95/21,153 |
| I.1E-4 | CH$_3$ | C$_6$H$_5$ | CH$_2$CH$_3$ | WO-A 95/21,153 |

TABLE I.1E-continued

Compounds of the formula IA, in which Q is phenyl, R' is
—C(CO$_2$CH$_3$)=CHOCH$_3$, n has the value 0, R" is
CH$_2$ON=CR$^\gamma$R$^\delta$=NOR$^\epsilon$, where R$^\gamma$, R$^\delta$ and
R$^\epsilon$ have the following meanings

| No. | R$^\gamma$ | R$^\delta$ | R$^\epsilon$ | Reference |
|---|---|---|---|---|
| I.1E-5 | CH$_3$ | 4-Cl—C$_6$H$_4$ | CH$_3$ | WO-A 95/21,153 |
| I.1E-6 | CH$_3$ | 4-Cl—C$_6$H$_4$ | CH$_2$CH$_3$ | WO-A 95/21,153 |

TABLE I.2A

Compounds of the formula IA, in which Q is phenyl, R' is
—C(CO$_2$CH$_3$)=NOCH$_3$, n has the value 0, R" is
unsubst. or subst. (het)aryloxymethylene, where the unsubst. or
subst. (het)aryl group has the following meanings

| No. | Unsubst. or subst. (het)aryl | Reference |
|---|---|---|
| I.2A-1 | 2-CH$_3$—C$_6$H$_4$ | EP-A 253 213 |
| I.2A-2 | 2,5-(CH$_3$)$_2$—C$_6$H$_3$ | EP-A 400 417 |
| I.2A-3 | 2,4-(CH$_3$)$_2$—C$_6$H$_3$ | EP-A 400 417 |
| I.2A-4 | 2,3,5-(CH$_3$)$_3$—C$_6$H$_2$ | EP-A 400 417 |
| I.2A-5 | 2-Cl, 5-CH$_3$—C$_6$H$_3$ | EP-A 400 417 |
| I.2A-6 | 2-CH$_3$, 4-C[CH$_3$]=NOCH$_3$—C$_6$H$_3$ | EP-A 386 561 |

TABLE I.2B

Compounds of the formula IA, in which Q is phenyl, R' is
—C(CO$_2$CH$_3$)=NOCH$_3$, n has the value 0, R" is
unsubst. or subst. (het)aryloxy, where the unsubst. or
subst. (het)aryl group has the following meanings

| No. | Unsubst. or subst. (het)aryl | Reference |
|---|---|---|
| I.2B-1 | C$_6$H$_5$ | EP-A 253 213 |
| I.2B-2 | 6-[2-CN—C$_6$H$_4$—O]-pyrimidin-4-yl | EP-A 468 684 |

TABLE I.2C

Compounds of the formula IA, in which Q is phenyl, R' is
—C(CO$_2$CH$_3$)=NOCH$_3$, n has the value 0, R" is
CH$_2$ON=CR$^\alpha$R$^\beta$, where R$^\alpha$ and R$^\beta$ have the following meanings

| No. | R$^\alpha$ | R$^\beta$ | Reference |
|---|---|---|---|
| I.2C-1 | CH$_3$ | 4-Cl—C$_6$H$_4$ | EP-A 463 488 |
| I.2C-2 | CH$_3$ | 3-Cl—C$_6$H$_4$ | EP-A 463 488 |
| I.2C-3 | CH$_3$ | 4-CF$_3$—C$_6$H$_4$ | EP-A 463 488 |
| I.2C-4 | CH$_3$ | 3-CF$_3$—C$_6$H$_4$ | EP-A 463 488 |
| I.2C-5 | CH$_3$ | 4-CH$_3$—C$_6$H$_4$ | EP-A 463 488 |
| I.2C-6 | CH$_3$ | 4-OCH$_2$CH$_3$-pyrimidin-2-yl | EP-A 472 300 |
| I.2C-7 | CH$_3$ | 3,5-Cl$_2$—C$_6$H$_3$ | EP-A 463 488 |

TABLE I.2D

Compounds of the formula IA, in which Q is phenyl, R' is
—C(CO$_2$CH$_3$)=NOCH$_3$, n has the value 0, R" is
CH$_2$ON=CR$^\gamma$CR$^\delta$=NOR$^\epsilon$, where
R$^\gamma$, R$^\delta$ and R$^\epsilon$ have the following meanings

| No. | R$^\gamma$ | R$^\delta$ | R$^\epsilon$ | Reference |
|---|---|---|---|---|
| I.2D-1 | CH$_3$ | CH$_3$ | CH$_3$ | WO-A 95/21,153 |
| I.2D-2 | CH$_3$ | CH$_3$ | CH$_2$CH$_3$ | WO-A 95/21,153 |
| I.2D-3 | CH$_3$ | C$_6$H$_5$ | CH$_3$ | WO-A 95/21,153 |
| I.2D-4 | CH$_3$ | C$_6$H$_5$ | CH$_2$CH$_3$ | WO-A 95/21,153 |
| I.2D-5 | CH$_3$ | 4-Cl—C$_6$H$_4$ | CH$_3$ | WO-A 95/21,153 |
| I.2D-6 | CH$_3$ | 4-Cl—C$_6$H$_4$ | CH$_2$CH$_3$ | WO-A 95/21,153 |

TABLE I.3A

Compounds of the formula IA, in which Q is phenyl, R' is
—C(CONHCH$_3$)=NOCH$_3$, n has the value 0, R" is unsubst. or subst.
(het)aryloxymethylene, where the unsubst. or subst. (het)aryl
group has the following meanings

| No. | Unsubst. or subst. (het)aryl | Reference |
|---|---|---|
| I.3A-1 | 2-CH$_3$—C$_6$H$_4$ | EP-A 477 631 |
| I.3A-2 | 2,5-(CH$_3$)$_2$—C$_6$H$_3$ | EP-A 477 631 |
| I.3A-3 | 2,4-(CH$_3$)$_2$—C$_6$H$_3$ | EP-A 477 631 |
| I.3A-4 | 2,3,5-(CH$_3$)$_3$—C$_6$H$_2$ | EP-A 477 631 |
| I.3A-5 | 2-CH$_3$, 4-C[CH$_3$]=NOCH$_3$—C$_6$H$_3$ | EP-A 579 124 |
| I.3A-6 | 1-[4-Cl—C$_6$H$_4$]-pyrazol-3-yl | EP-A 686 152 |
| I.3A-7 | 1-[2,4-Cl$_2$—C$_6$H$_3$]-pyrazol-3-yl | EP-A 686 152 |

TABLE I.3B

Compounds of the formula IA, in which Q is phenyl, R' is
—C(CONHCH$_3$)=NOCH$_3$, n has the value 0, R" is unsubst. or subst.
(het)aryloxy, where the unsubst. or subst. (het)aryl group has
the following meanings

| No. | Unsubst. or subst. (het)aryl | Reference |
|---|---|---|
| I.3B-1 | C$_6$H$_5$ | EP-A 398 692 |
| I.3B-2 | 6-[2-CN—C$_6$H$_4$—O]-pyrimidin-4-yl | GB-A 2 253 624 |

TABLE I.3C

Compounds of the formula IA, in which Q is phenyl, R' is
—C(CONHCH$_3$)=NOCH$_3$, n has the value 0, R" is unsubst. or subst.
(het)arylethenylene, where the unsubst. or subst. (het)aryl group
has the following meanings

| No. | Unsubst. or subst. (het)aryl | Reference |
|---|---|---|
| I.3C-1 | 1-[2,4-Cl$_2$—C$_6$H$_3$], 5-CF$_3$-pyrazol-4-yl | EP-A 691 332 |

TABLE I.3D

Compounds of the formula IA, in which Q is phenyl, R' is
—C(CONHCH$_3$)=NOCH$_3$, n has the value 0, R" is CH$_2$ON=CR$^\alpha$R$^\beta$,
where R$^\alpha$ and R$^\beta$ have the following meanings

| No. | R$^\alpha$ | R$^\beta$ | Reference |
|---|---|---|---|
| I.3D-1 | CH$_3$ | 4-Cl—C$_6$H$_4$ | EP-A 463 488 |
| I.3D-2 | CH$_3$ | 3-Cl—C$_6$H$_4$ | EP-A 463 488 |
| I.3D-3 | CH$_3$ | 4-CF$_3$—C$_6$H$_4$ | EP-A 585 751 |
| I.3D-4 | CH$_3$ | 3-CF$_3$—C$_6$H$_4$ | EP-A 585 751 |
| I.3D-5 | CH$_3$ | 4-CH$_3$—C$_6$H$_4$ | EP-A 463 488 |
| I.3D-6 | CH$_3$ | 3,5-Cl$_2$—C$_6$H$_3$ | EP-A 463 488 |
| I.3D-7 | CH$_3$ | 2-OCH$_2$CH$_3$-pyrimidin-2-yl | WO-A 92/13,830 |

TABLE I.3E

Compounds of the formula IA, in which Q is phenyl, R' is
—C(CONHCH$_3$)=NOCH$_3$, n has the value 0, R" is
CH$_2$ON=CR$^\gamma$CR$^\delta$=NOR$^\epsilon$, where R$^\gamma$, R$^\delta$ and R$^\epsilon$
have the following meanings

| No. | R$^\gamma$ | R$^\delta$ | R$^\epsilon$ | Reference |
|---|---|---|---|---|
| I.3E-1 | CH$_3$ | CH$_3$ | CH$_3$ | WO-A 95/21,154 |
| I.3E-2 | CH$_3$ | CH$_3$ | CH$_2$CH$_3$ | WO-A 95/21,154 |
| I.3E-3 | CH$_3$ | C$_6$H$_5$ | CH$_3$ | WO-A 95/21,154 |
| I.3E-4 | CH$_3$ | C$_6$H$_5$ | CH$_2$CH$_3$ | WO-A 95/21,154 |

TABLE I.3E-continued

Compounds of the formula IA, in which Q is phenyl, R' is —C(CONHCH$_3$)=NOCH$_3$, n has the value 0, R" is CH$_2$ON=CR$^\gamma$CR$^\delta$=NOR$^\epsilon$, where R$^\gamma$, R$^\delta$ and R$^\epsilon$ have the following meanings

| No. | R$^\gamma$ | R$^\delta$ | R$^\epsilon$ | Reference |
|---|---|---|---|---|
| I.3E-5 | CH$_3$ | 4-Cl—C$_6$H$_4$ | CH$_3$ | WO-A 95/21,154 |
| I.3E-6 | CH$_3$ | 4-Cl—C$_6$H$_4$ | CH$_2$CH$_3$ | WO-A 95/21,154 |

TABLE I.4A

Compounds of the formula IA, in which Q is phenyl, R' is —C(CO$_2$CH$_3$)=CHCH$_3$, n has the value 0, R" is unsubst. or subst. (het)aryloxymethylene, where the unsubst. or subst. (het)aryl group has the following meanings

| No. | Unsubst. or subst. (het)aryl | Reference |
|---|---|---|
| I.4A-1 | 2-CH$_3$—C$_6$H$_4$ | EP-A 280 185 |
| I.4A-2 | 2,5-(CH$_3$)$_2$—C$_6$H$_3$ | EP-A 513 580 |
| I.4A-3 | 2,4-(CH$_3$)$_2$—C$_6$H$_3$ | EP-A 513 580 |
| I.4A-4 | 2,3,5-(CH$_3$)$_3$—C$_6$H$_2$ | EP-A 513 580 |
| I.4A-5 | 2-Cl, 5-CH$_3$—C$_6$H$_3$ | EP-A 513 580 |
| I.4A-6 | 2-CH$_3$, 4-C[CH$_3$]=NOCH$_3$—C$_6$H$_3$ | EP-A 513 580 |
| I.4A-7 | 1-[4-Cl—C$_6$H$_4$]-pyrazol-3-yl | WO-A 95/29,896 |

TABLE I.4B

Compounds of the formula IA, in which Q is phenyl, R' is —C(CO$_2$CH$_3$)=CHCH$_3$, n has the value 0, R" is unsubst. or subst. (het)aryloxy, where the unsubst. or subst. (het)aryl group has the following meanings

| No. | Unsubst. or subst. (het)aryl | Reference |
|---|---|---|
| I.4B-1 | C$_6$H$_5$ | EP-A 513 580 |

TABLE I.4C

Compounds of the formula IA, in which Q is phenyl, R' is —C(CO$_2$CH$_3$)=CHCH$_3$, n has the value 0, R" is CH$_2$ON=CR$^\gamma$CR$^\delta$=NOR$^\epsilon$, where R$^\gamma$, R$^\delta$ and R$^\epsilon$ have the following meanings

| No. | R$^\gamma$ | R$^\delta$ | R$^\epsilon$ | Reference |
|---|---|---|---|---|
| I.4C-1 | CH$_3$ | CH$_3$ | CH$_3$ | WO-A 95/21,153 |
| I.4C-2 | CH$_3$ | CH$_3$ | CH$_2$CH$_3$ | WO-A 95/21,153 |
| I.4C-3 | CH$_3$ | C$_6$H$_5$ | CH$_3$ | WO-A 95/21,153 |
| I.4C-4 | CH$_3$ | C$_6$H$_5$ | CH$_2$CH$_3$ | WO-A 95/21,153 |
| I.4C-5 | CH$_3$ | 4-Cl—C$_6$H$_4$ | CH$_3$ | WO-A 95/21,153 |
| I.4C-6 | CH$_3$ | 4-Cl—C$_6$H$_4$ | CH$_2$CH$_3$ | WO-A 95/21,153 |

TABLE I.5A

Compounds of the formula IA, in which Q is phenyl, R' is —C(CO$_2$CH$_3$)=CHCH$_2$CH$_3$, n has the value 0, R" is unsubst. or subst. (het)aryloxymethylene, where the unsubst. or subst. (het)aryl group has the following meanings

| No. | Unsubst. or subst. (het)aryl | Reference |
|---|---|---|
| I.5A-1 | 2-CH$_3$—C$_6$H$_4$ | EP-A 513 580 |
| I.5A-2 | 2,5-(CH$_3$)$_2$—C$_6$H$_3$ | EP-A 513 580 |
| I.5A-3 | 2,4-(CH$_3$)$_2$—C$_6$H$_3$ | EP-A 513 580 |
| I.5A-4 | 2,3,5-(CH$_3$)$_3$—C$_6$H$_2$ | EP-A 513 580 |
| I.5A-5 | 2-Cl, 5-CH$_3$—C$_6$H$_3$ | EP-A 513 580 |
| I.5A-6 | 2-CH$_3$, 4-C[CH$_3$]=NOCH$_3$—C$_6$H$_3$ | EP-A 513 580 |

TABLE I.5B

Compounds of the formula IA, in which Q is phenyl, R' is —C(CO$_2$CH$_3$)=CHCH$_2$CH$_3$, n has the value 0, R" is unsubst. or subst. (het)aryloxy, where the unsubst. or subst. (het)aryl group has the following meanings

| No. | Unsubst. or subst. (het)aryl | Reference |
|---|---|---|
| I.5B-1 | C$_6$H$_5$ | EP-A 513 580 |

TABLE I.5C

Compounds of the formula IA, in which Q is phenyl, R' is —C(CO$_2$CH$_3$)=CHCH$_2$CH$_3$, n has the value 0, R" is CH$_2$ON=CR$^\gamma$CR$^\delta$=NOR$^\epsilon$, where R$^\gamma$, R$^\delta$ and R$^\epsilon$ have the following meanings

| No. | R$^\gamma$ | R$^\delta$ | R$^\epsilon$ | Reference |
|---|---|---|---|---|
| I.5C-1 | CH$_3$ | CH$_3$ | CH$_3$ | WO-A 95/21,153 |
| I.5C-2 | CH$_3$ | CH$_3$ | CH$_2$CH$_3$ | WO-A 95/21,153 |
| I.5C-3 | CH$_3$ | C$_6$H$_5$ | CH$_3$ | WO-A 95/21,153 |
| I.5C-4 | CH$_3$ | C$_6$H$_5$ | CH$_2$CH$_3$ | WO-A 95/21,153 |
| I.5C-5 | CH$_3$ | 4-Cl—C$_6$H$_4$ | CH$_3$ | WO-A 95/21,153 |
| I.5C-6 | CH$_3$ | 4-Cl—C$_6$H$_4$ | CH$_2$CH$_3$ | WO-A 95/21,153 |

TABLE I.6A

Compounds of the formula IA, in which Q is phenyl, R' is —C(COCH$_3$)=NOCH$_3$, n has the value 0, R" is unsubst. or subst. (het)aryloxymethylene, where the unsubst. or subst. (het)aryl group has the following meanings

| No. | Unsubst. or subst. (het)aryl | Reference |
|---|---|---|
| I.6A-1 | 2-CH$_3$—C$_6$H$_4$ | EP-A 498 188 |
| I.6A-2 | 2,5-(CH$_3$)$_2$—C$_6$H$_3$ | EP-A 498 188 |
| I.6A-3 | 2,4-(CH$_3$)$_2$—C$_6$H$_3$ | EP-A 498 188 |
| I.6A-4 | 2,3,5-(CH$_3$)$_3$—C$_6$H$_2$ | EP-A 498 188 |
| I.6A-5 | 2-CH$_3$, 4-C[CH$_3$]=NOCH$_3$—C$_6$H$_3$ | EP-A 498 188 |

TABLE I.6B

Compounds of the formula IA, in which Q is phenyl, R' is —C(COCH$_3$)=NOCH$_3$, n has the value 0, R" is unsubst. or subst. (het)aryloxy, where the unsubst. or subst. (het)aryl group has the following meanings

| No. | Unsubst. or subst. (het)aryl | Reference |
|---|---|---|
| I.6B-1 | C$_6$H$_5$ | EP-A 498 188 |
| I.6B-2 | 6-[2-CN—C$_6$H$_4$—O]-pyrimidin-4-yl | EP-A 498 188 |

TABLE I.7A

Compounds of the formula IA, in which Q is phenyl, R' is —C(COCH$_2$CH$_3$)=NOCH$_3$, n has the value 0, R" is unsubst. or subst. (het)aryloxymethylene, where the unsubst. or subst. (het)aryl group has the following meanings

| No. | Unsubst. or subst. (het)aryl | Reference |
|---|---|---|
| I.7A-1 | 2-CH$_3$—C$_6$H$_4$ | EP-A 498 188 |
| I.7A-2 | 2,5-(CH$_3$)$_2$—C$_6$H$_3$ | EP-A 498 188 |
| I.7A-3 | 2,4-(CH$_3$)$_2$—C$_6$H$_3$ | EP-A 498 188 |
| I.7A-4 | 2,3,5-(CH$_3$)$_3$—C$_6$H$_2$ | EP-A 498 188 |
| I.7A-5 | 2-CH$_3$, 4-C[CH$_3$]=NOCH$_3$—C$_6$H$_3$ | EP-A 498 188 |

TABLE I.7B

Compounds of the formula IA, in which Q is phenyl, R' is
—C(COCH$_2$CH$_3$)=NOCH$_3$, n has the value 0, R" is unsubst. or subst.
(het)aryloxy, where the unsubst. or subst. (het)aryl group has
the following meanings

| No. | Unsubst. or subst. (het)aryl | Reference |
|---|---|---|
| I.7B-1 | C$_6$H$_5$ | EP-A 498 188 |
| I.7B-2 | 6-[2-CN—C$_6$H$_4$—O]-pyrimidin-4-yl | EP-A 498 188 |

TABLE I.8A

Compounds of the formula IA, in which Q is phenyl, R' is
—N(OCH$_3$)—CO$_2$CH$_3$, n has the value 0, R" is unsubst. or subst.
(het)aryloxymethylene, where the unsubst. or subst. (het)aryl
group has the following meanings

| No. | Unsubst. or subst. (het)aryl | Reference |
|---|---|---|
| I.8A-1 | 2-CH$_3$—C$_6$H$_4$ | WO-A 93/15,046 |
| I.8A-2 | 2,5-(CH$_3$)$_2$—C$_6$H$_3$ | WO-A 93/15,046 |
| I.8A-3 | 2,4-(CH$_3$)$_2$—C$_6$H$_3$ | WO-A 93/15,046 |
| I.8A-4 | 2,3,5-(CH$_3$)$_3$—C$_6$H$_2$ | WO-A 93/15,046 |
| I.8A-5 | 2-Cl, 5-CH$_3$—C$_6$H$_3$ | WO-A 93/15,046 |
| I.8A-6 | 2-CH$_3$, 4-C[CH$_3$]=NOCH$_3$—C$_6$H$_3$ | WO-A 93/15,046 |
| I.8A-7 | 2-CH$_3$, 4-C[CH$_3$]=NOCH$_3$CH$_3$—C$_6$H$_3$ | WO-A 93/15,046 |
| I.8A-8 | 2-CH$_3$, 4-C[CH$_2$CH$_3$]=NOCH$_3$—C$_6$H$_3$ | WO-A 93/15,046 |
| I.8A-9 | 2-CH$_3$, 4-C[CH$_2$CH$_3$]=NOCH$_3$CH$_3$—C$_6$H$_3$ | WO-A 93/15,046 |
| I.8A-10 | 1-[4-Cl—C$_6$H$_4$]-pyrazol-3-yl | WO-A 96/01,256 |

TABLE I.8B

Compounds of the formula IA, in which Q is phenyl, R' is
—N(OCH$_3$)—CO$_2$CH$_3$, n has the value 0, R" is CH$_2$ON=CR$^\alpha$R$^\beta$,
where R$^\alpha$ and R$^\beta$ have the following meanings

| No. | R$^\alpha$ | R$^\beta$ | Reference |
|---|---|---|---|
| I.8B-1 | CH$_3$ | 3,5-Cl$_2$—C$_6$H$_3$ | WO-A 93/15,046 |

It is to be assumed according to previous knowledge that the effect according to the invention of the control of fish mycoses and single-cell ectoparasites in fish can be employed in all fish populations, in particular in breeding ponds, breeding tanks and aquaria, natural game fish waters and marine fish farms.

The compositions according to the invention are particularly suitable for treating Cyprinidae, Percidae and Salmonidae and other breeding and ornamental fish.

In particular, the compositions according to the invention are suitable for controlling branchiomycosis and saprolegniasis in fish, and their egg, larval and juvenile stages.

The compositions according to the invention are furthermore suitable for controlling, in particular, single-cell ectoparasites on fish, the following being mentioned by way of example: Ichthyophthirius sp., Chilodonella sp., Trichodina sp. and Ichthyobodo.

The symptoms of costiasis caused by such parasites can be controlled by the active compounds of the formulae IA, IB and IC according to the invention.

The application rates of compounds I.A and I.B are, depending on the type and development stage of the fish, from 0.1 µg/l to 5 mg/l, preferably 0.3 µg/l to 3 mg/l, in particular 1 µg/l to 1 mg/l, particularly preferably 5 µg/l to 500 µg/l. Higher concentrations are generally not necessary, but can be useful in the treatment of egg, larval and juvenile stages, depending on the type of compound, particularly in artificial systems (eg. breeding tanks or aquaria).

The compounds I.A and I.B can be used directly or mixed with customary inert carriers before use. Those substances are fundamentally suitable as inert carriers which facilitate or guarantee a homogeneous distribution of the active compound in the water.

The compositions are prepared in a known manner, eg. by extending the active compound with solvents and/or carriers, if desired using emulsifiers and dispersants, where if water is used as a diluent other organic solvents can also be used as auxiliary solvents.

Suitable auxiliaries for this purpose are essentially:

solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water;

carriers such as ground natural minerals (eg. kaolins, argilaceous earths, talc, chalk) and ground synthetic minerals (eg. highly disperse silica, silicates);

emulsifiers such as nonionic and anionic emulsifiers (eg. polyoxyethylene fatty alcohol ethers, alkylsulfonates and arylsulfonates) and dispersants such as lignin sulfite waste liquors and methylcellulose.

Suitable surface-active substances are the alkali metal, alkaline earth metal or ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl, lauryl ether and fatty alcohol sulfates, and also salts of sulfated hexa-, hepta- and octadecanols, as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenyl ether, ethoxylated isooctyl-, octyl- or nonylphenol, alkylphenyl or tributylphenyl polyglycol ether, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Aqueous application forms can be prepared from emulsion concentrates, dispersions, pastes, wettable powders or water-dispersible granules by addition of water. To prepare emulsions, pastes or oil dispersions, the substances can be homogenized as such, or dissolved in an oil or solvent, by means of wetting agents, adherents, dispersants or emulsifiers. However, concentrates consisting of active substance, wetting agent, adherent, dispersant or emulsifier and possibly solvent or oil which are suitable for dilution with water can also be prepared.

Powder, broadcasting and dusting compositions can be prepared by mixing or joint grinding of the active substances with a solid carrier.

Granules, eg. coated, impregnated and homogeneous granules can be prepared by binding the active compounds to solid carriers.

Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas, and vegetable products, such as grain meal, tree bark, wood and nutshell meal, cellulose powder or other solid carriers. The active compound concentrations in the ready-to-use preparations can be varied within relatively wide ranges.

Very generally, the compositions contain from 0.0001 to 95% by weight of active compound.

Formulations containing more than 95% by weight of active compound can be applied with great success in the ultra-low volume process (ULV), in which the active compound can be used even without additives.

The active compounds are normally employed in a purity of from 90% to 100%, preferably 95% to 100% (according to NMR spectrum).

It was possible to show the action for controlling fish mycoses by means of the following tests.

During investigations in small stretches of water for the ecotoxicological estimation of fungicidal crop protection agents, fish were also tested. Groups of 7 animals in each case of the species Cyprinus carpio were kept under open air conditions in four containers filled with 6.5 m$^3$ of a natural beta-mesosaprobic water and natural sediment. One container served as the control, the others were treated with various concentrations of the active compound I.2A-1 (corresponds to I.01 of the following table): 0; 1.3 μg/l; 6.7 μg/l and 33.3 μg/l.

The active compounds were used here as 50% by weight water-dispersible granules of the following composition:
  50% by weight of active compound
  10% by weight of carrier (ammonium sulfate)
  1% by weight of Pluronic® PE 6800 (adduct of ethylene oxide and polypropylene glycol, dispersant)
  0.84% by weight of antifoam (33% strength aqueous emulsion of polydimethylsiloxane)
made up to 100% by weight with a 2:1 mixture of
  sodium lignosulfonate and
  the sodium salt of the formaldehyde condensate of naphthalenesulfonic acid.

The randomly distributed fish were put in on 04.25.94. On 05.03.94 a fungicide treatment of the reservoirs was carried out. In the further course of the test, 4 of 7 fish in the control reservoirs (no fungicide treatment) became ill and died of fungal attack, no fish (but 2 before treatment) became ill and died at the lowest concentration and likewise none of the fish became ill and died at the two higher concentrations.

That is to say whereas in the control a good half of the fish were affected by fungi and also died thereof, in the reservoirs treated with I.01 no fungal attack occurred. All fish remained healthy.

At the end of the test after several treatments, the growth in size of the fish and their general state of health was checked. During the course of this, no negative effects of the fungicide whatsoever were found on the fish.

We claim:

1. A method for controlling fish mycoses and single-cell ectoparasites of fish, which comprises applying to fish or their habitat an effective amount of compound suitable for inhibiting the mitochondrial respiratory chain at the stage of the b/c$_1$ of the formula IA or IB

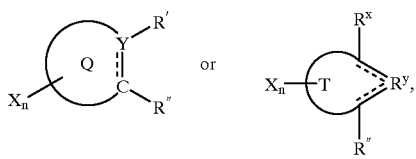

is used where ___ is a single or double bond and the index and the substituents have the following meanings:

R' is —C[CO$_2$CH$_3$]=CHOCH$_3$, —C[CO$_2$CH$_3$]=NOCH$_3$, —C[CONHCH$_3$]=—NOCH$_3$, —C[CO$_2$CH$_3$]=CHCH$_3$, —C[CO$_2$CH$_3$]=CHCH$_2$CH$_3$, —C[COCH$_3$]=NOCH$_3$, —C[COCH$_2$CH$_3$]=NOCH$_3$, —N(OCH$_3$)—CO$_2$CH$_3$, —N(CH$_3$)—CO$_2$CH$_3$, —N(CH$_2$CH$_3$)—CO$_2$CH$_3$,

R" is a C-organic radical,
  a C-organic radical which is bonded directly or via an oxy, mercapto, amino or alkylamino group, or
  together with a group X and the ring Q or T, to which they are bonded, are an unsubst. or subst. bicyclic, partially or completely unsaturated system which, in addition to carbon ring members, can contain heteroatoms from the group consisting of oxygen, sulfur and nitrogen, R$^x$ is —OC[CO$_2$CH$_3$]=CHOCH$_3$, —OC[CO$_2$CH$_3$]=CHCH$_3$, —OC[CO$_2$CH$_3$]=CHCH$_2$CH$_3$, —SC[CO$_2$CH$_3$]=CHOCH$_3$, —SC[CO$_2$CH$_3$]=CHCH$_3$, —SC[CO$_2$CH$_3$]=CHCH$_2$CH$_3$, —N(CH$_3$)C[CO$_2$CH$_3$]=CHOCH$_3$, —N(CH$_3$)C[CO$_2$CH$_3$]=NOCH$_3$, —CH$_2$C[CO$_2$CH$_3$]=CHOCH$_3$, —CH$_2$C[CO$_2$CH$_3$]=NOCH$_3$, —CH$_2$C[CONHCH$_3$]=NOCH$_3$, R$^y$ is oxygen, sulfur, =CH— or =N—, n is 0, 1, 2 or 3, where the radicals X can be different if n>1;

X is cyano, nitro, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio or, in the case where n>1, a C$_3$–C$_5$-alkylene, C$_3$–C$_5$-alkenylene, oxy-C$_2$–C$_4$-alkylene, oxy-C$_1$–C$_3$-alkylanoxy, oxy-C$_2$–C$_4$-alkenylene, oxy-C$_2$–C$_4$-alkenylenoxy or butadienediyl group bonded to two adjacent C atoms of the phenyl ring, where these chains in turn can carry one to three of the following radicals: halogen, C$_1$–C$_4$-alkyl, C$_1$–C$_4$-haloalkyl, C$_1$–C$_4$-alkoxy, C$_1$–C$_4$-haloalkoxy or C$_1$–C$_4$-alkylthio, Y is =C— or —N—, Q is phenyl, pyrrolyl, thienyl, furyl, pyrazolyl, imidazolyl, oxazolyl, isoxazolyl, thiazolyl, thiadiazolyl, triazolyl, pyridinyl, 2-pyridonyl, pyrimidinyl or tridzinyl, T is phenyl, oxazolyl, thiazolyl, thiadiazolyl, oxadiazolyl, pyridinyl, pyrimidinyl or triazinyl.

2. A method for controlling fish mycoses and single-cell ectoparasites of fish, which comprises applying to fish or their habitat an effective amount of a compound suitable for inhibiting the mitochondrial respiratory chain at the stage of the b/c$_1$ of the formula IC

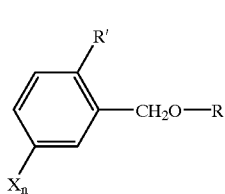

is used where the index and the substituents have the following meanings:

x is cyano, nitro, halogen, C$_1$–C$_4$-alkyl, C$_1$–C$_4$-haloalkyl, C$_1$–C$_4$-alkoxy, C$_1$–C$_4$-haloalkoxy or C$_1$–C$_4$-alkylthio;

n is 0, 1, 2 or 3, where the radicals x can be different if the value of n is greater than 1;

R' is C[CO$_2$CH$_3$]=CHOCH$_3$, C[CO$_2$CH$_3$]=NOCH$_3$, C[CONHCH$_3$]=NOCH$_3$, C[COCH$_2$CH$_3$]=NOCH$_3$ or N(OCH$_3$)—CO$_2$CH$_3$;

R is phenyl, pyrazolyl, pyridyl or pyrimidyl, where these groups can be partially or completely halogenated and/or can carry one to three of the following radicals: cyano, nitro, $C_1-C_4$-alkyl, $C_3-C_6$-cycloalkyl, $C_1-C_4$-haloalkyl, $C_1-C_4$-alkoxy, $C_1-C_4$-haloalkoxy and $C_1-C_6$-alkylthio and/or a $CR^1=NOR^2$ group or a phenyl ring which in turn can be partially or completely halogenated and/or can carry one to three of the following radicals: cyano, nitro, $C_1-C_4$-alkyl, $C_3-C_6$-cycloalkyl, $C_1-C_4$-haloalkyl, $C_1-C_4$-alkoxy, $C_1-C_4$-haloalkoxy and $C_1-C_6$-alkylthio;

$N=CR^\alpha R^\beta$ or $N=CR^\gamma CR^\delta=NOR^\epsilon$;

$R^1$, $R^2$, $R^\alpha$, $R^\gamma$ and $R^\epsilon$ are $C_1-C_4$-alkyl, $R^\beta$ is phenyl, pyridyl or pyrimidyl, where these groups can be partially or completely halogenated and/or can carry one to three of the following radicals: cyano, nitro, $C_1-C_4$-alkyl, $C_3-C_6$-cycloalkyl, $C_1-C_4$-haloalkyl, $C_1-C_4$-alkoxy, $C_1-C_4$-haloalkoxy and $C_1-C_6$-alkylthio;

$R^\delta$ is $C_1-C_4$-alkyl or phenyl, which can be partially or completely halogenated and/or can carry one to three of the following radicals: cyano, nitro, $C_1-C_4$-alkyl, $C_3-C_6$-cycloalkyl, $C_1-C_4$-haloalkyl, $C_1-C_4$-alkoxy, $C_1-C_4$-haloalkoxy and $C_1-C_6$-alkylthio and/or a $CR^1=NOR^2$ group.

* * * * *

UNITED STATES PATENT AND TRADEMARK OFFICE
CERTIFICATE OF CORRECTION

PATENT NO. : 6,075,023

DATED : June 13, 2000

INVENTOR(S) : DOHMEN et al.

It is certified that error appears in the above-indentified patent and that said Letters Patent is hereby corrected as shown below:

Col. 13, claim 1, line 54, delete "of the".

Col. 13, claim 1, line 67, "-C[CONHCH$_3$]=-NOCH$_3$," should be -- -C[CONHCH$_3$]=NOCH$_3$, --.

Col. 14, claim 1, line 28, "alkylanoxy" should be --alkylenoxy--.

Col. 14, claim 1, line 38, "tridzinyl" should be --triazinyl--.

Col. 14, claim 2, line 61, "x" should be --X--.

Signed and Sealed this

Twenty-seventh Day of March, 2001

Attest:

NICHOLAS P. GODICI

Attesting Officer

Acting Director of the United States Patent and Trademark Office